United States Patent [19]

Gruner

[11] Patent Number: 5,634,466
[45] Date of Patent: Jun. 3, 1997

[54] ULTRASONIC TRANSESOPHAGEAL PROBE WITH DETACHABLE TRANSDUCER TIP

[75] Inventor: George P. Gruner, Mukilteo, Wash.

[73] Assignee: Advanced Technology Laboratories, Inc., Bothell, Wash.

[21] Appl. No.: 572,807

[22] Filed: Dec. 15, 1995

Related U.S. Application Data

[62] Division of Ser. No. 375,023, Jan. 19, 1995, Pat. No. 5,479,930, which is a division of Ser. No. 155,416, Nov. 19, 1993, Pat. No. 5,402,793.

[51] Int. Cl.⁶ ........................................................ A61B 8/12
[52] U.S. Cl. ............................... 128/662.06; 128/602.03; 600/136
[58] Field of Search ........................... 128/660.09, 660.1, 128/661.08, 662.01, 662.03–662.06; 600/129, 132, 136

[56] References Cited

U.S. PATENT DOCUMENTS

| | | | |
|---|---|---|---|
| 3,948,251 | 4/1976 | Hosono | 128/4 |
| 4,149,419 | 4/1979 | Connell, Jr. et al. | 128/660.1 X |
| 4,494,549 | 1/1985 | Namba et al. | 128/662.06 |
| 4,543,960 | 10/1985 | Harui et al. | 128/660 |
| 5,085,221 | 2/1992 | Ingebrigtsen et al. | 128/660 |
| 5,179,935 | 1/1993 | Miyagi | 128/4 |
| 5,181,514 | 1/1993 | Solomon et al. | 128/660 |
| 5,195,519 | 3/1993 | Angelsen | 128/662.06 X |
| 5,351,691 | 10/1994 | Brommersma | 128/662.06 |

OTHER PUBLICATIONS

Baba, K. "Ultrasonic Scanner for Exam of Coeliac Cavity", Ep 0 028 825 published May 20, 1981 (copy 128/662.060).

*Primary Examiner*—Francis Jaworski
*Attorney, Agent, or Firm*—W. Brinton Yorks, Jr.

[57] ABSTRACT

A multiplane TEE probe is provided for the imaging and diagnosis of multiple scan planes from within a cavity of the body. The probe includes an articulation section formed of a plurality of interconnected links. The articulation section is controlled from the handle of the probe, with the articulation limit stops located in the handle. The articulation section may be locked in a given bent position, but the lock will be overcome by the force of the esophagus against the transducer tip if the probe is withdrawn in a locked and bent position. When the articulation section is locked an indication signal is displayed on the handle of the probe and on the display of the ultrasound system.

16 Claims, 13 Drawing Sheets

ULTRASONIC TRANSESOPHAGEAL PROBE WITH DETACHABLE TRANSDUCER TIP

This is a division of United States patent application Ser. No. 08/375,023, filed Jan. 19, 1995, and now U.S. Pat. No. 5,479,930, which is a division of U.S. patent application Ser. No. 08/155,416, filed Nov. 19, 1993 and now U.S. Pat. No. 5,402,793.

This invention relates to probes for ultrasonic diagnostic systems which scan the body from within the patient's esophagus or stomach. In particular, the probes of the present invention are ideally suited for imaging in any one of a number of planar orientations, and are often referred to as multiplane TEE (transesophageal echocardiography) probes.

The heart is one organ for which ultrasonic diagnosis has always been difficult. This is because the heart is located in the thoracic cavity, surrounded by the ribs and lungs. Ultrasonic scanning through the ribs is not a viable option due to the absorptive and reflective characteristics of bone structure. Accordingly, the accepted clinical procedure is to scan the heart intercostally. But the transmission and reception of ultrasound through the intercostal windows is sometimes not clinically useful, because of acoustic reflections from normal body structures such as the cartilage connected to the ribs.

The advent of endoscopic technology whereby medical devices can be introduced into the body and manipulated external to the body, led to the development of a new technique for ultrasonically scanning the heart: transesophageal echocardiography. By this technique an ultrasonic transducer is located at the end of an elongated probe, which is passed through the patient's mouth and into the esophagus or stomach. From such a position within the thoracic cavity, the ribs no longer pose an impediment to the transmission and reception of ultrasound. The typical transesophageal scanhead includes a control mechanism external to the body, enabling the clinician to manipulate the end of the probe so that the transducer on the probe end is directed as desired toward the heart. This technique, which places the ultrasonic transducer in close proximity to the heart itself, has been found to be most effective in the diagnosis of disease conditions of the heart.

U.S. Pat. No. 4,543,960 (Harui et al.), the contents of which are incorporated herein by reference, describes a transesophageal echocardiographic (TEE) scanhead in which a phased array or linear array transducer is mounted on a rotating base inside the scanhead. As shown in the drawings of that patent, the array transducer is a square or rectangular shaped array of piezoelectric elements which is mounted on a cylindrical rotatable base. A pulley is mounted on a shaft extending from the rotatable base, whereby the base and transducer array may be rotated inside the scanhead. A control cable from the control unit of the scanhead passes around the pulley. As the control cable moves by control of the control unit the pulley and rotatable base are turned, thereby rotating the transducer array and hence the image plane. Improvements to the Harui et al. probe are described in U.S. Pat. No. 5,226,422 (McKeighen et al.), including a circular array transducer employing new grounding technique, a bell-shaped housing for the transducer, and a novel bubble trap for the transducer compartment.

In accordance with the principles of the present invention a number of improvements are described which improve the manufacture and performance of a TEE scanhead such as that of U.S. Pat. Nos. 4,543,960 and 5,226,422. The transducer of the scanhead is contained within a removable articulating tip that allows the physician to change transducers simply by replacing the tip of the probe. The articulation mechanism includes a plurality of links which snap together to form a continuous, torsionally stiff articulating joint. The joint has built in angulation stops and exhibits substantially no torsional play when loaded. The articulating joint can be locked in a given position by an articulation lock controlled from the handle of the probe, with limit stops of the articulating mechanism located in the handle instead of the tip. The status of the lock is indicated at the handle and on the screen of the ultrasonic imaging system. For patient safety the lock can be overridden by a relatively small force at the probe tip in the event the probe is removed from the patient's esophagus while the joint is locked in an articulated position. The transducer in the probe tip is rotated by a motor driven mechanism with two speeds of rotation, a relatively slow speed and a faster speed. Depressing both speed controls at once causes the transducer to rotate to its predetermined home orientation. The transducer employs a novel technique for dissipating heat which accumulates in the lens of the transducer.

Figure 1:
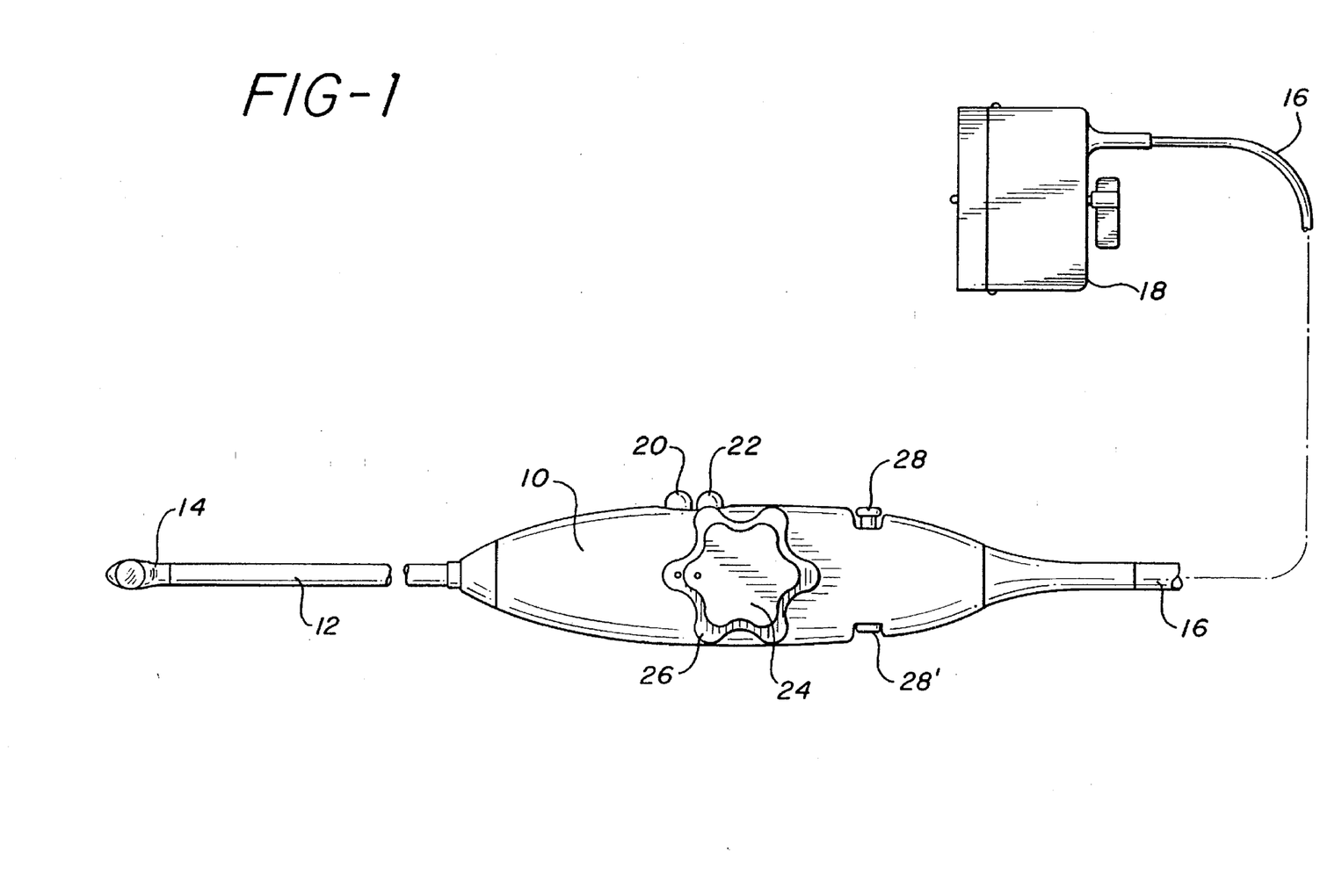
FIG. 1 illustrates a plan view of a multiplane TEE probe of the present invention.

Referring first to FIG. 1, a plan view of a multiplane TEE probe of the present invention is shown. The probe includes a handle 10 where the major controls of the probe are located. Extending from one end of the handle 10 is a gastroscope tube 12. The gastroscope tube is suitable for insertion into a body cavity such as the esophagus, and for TEE applications the tube is approximately 100 cm long. At the end of the gastroscope tube 12 is the distal tip 14 of the probe where the ultrasonic transducer is located.

Extending from the other end of the handle 10 is an electrical cable 16 which terminates at a connector 18. The connector 18 is suitable for connecting the probe to an ultrasound system which energizes the probe and displays images formed from the acoustic signals transmitted and received by the transducer at the tip of the probe.

Five of the probe controls are shown in FIG. 1. Two buttons 20 and 22 control the clockwise and counter clockwise rotation of the transducer at the tip of the probe. The probe tip can be articulated in any of four directions from the handle by the right-left articulation control knob 24 and the forward-back articulation control knob 26. Reciprocating brake buttons 28, 28' are used to lock and unlock the articulation control in any articulated position.

Figure 2A:
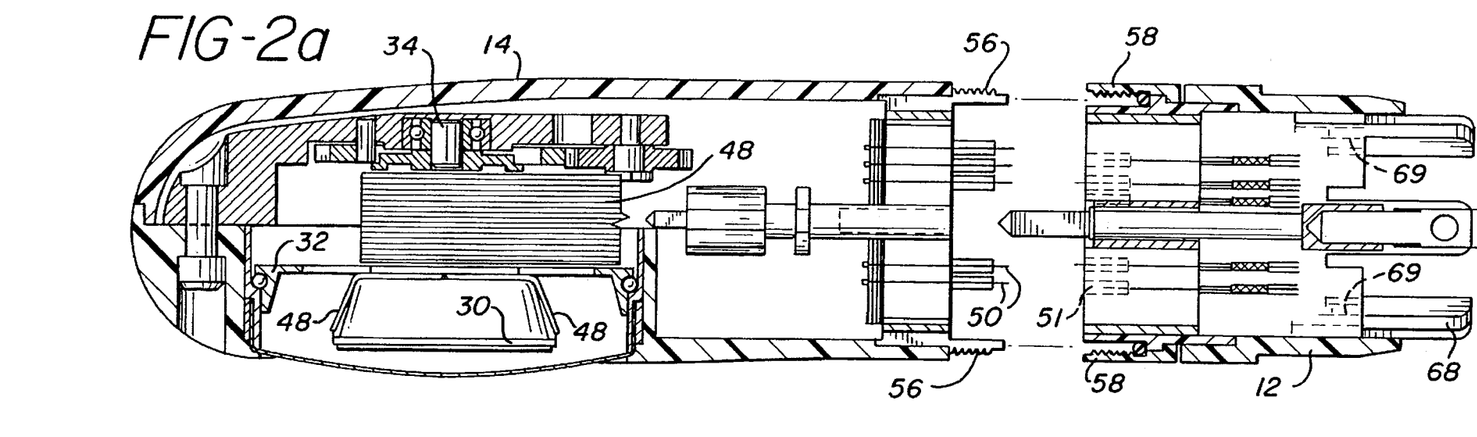
FIGS. 2a, 2b, 2c and 3 illustrate views of the distal tip of a multiplane TEE probe of the present invention.
Figure 2B:
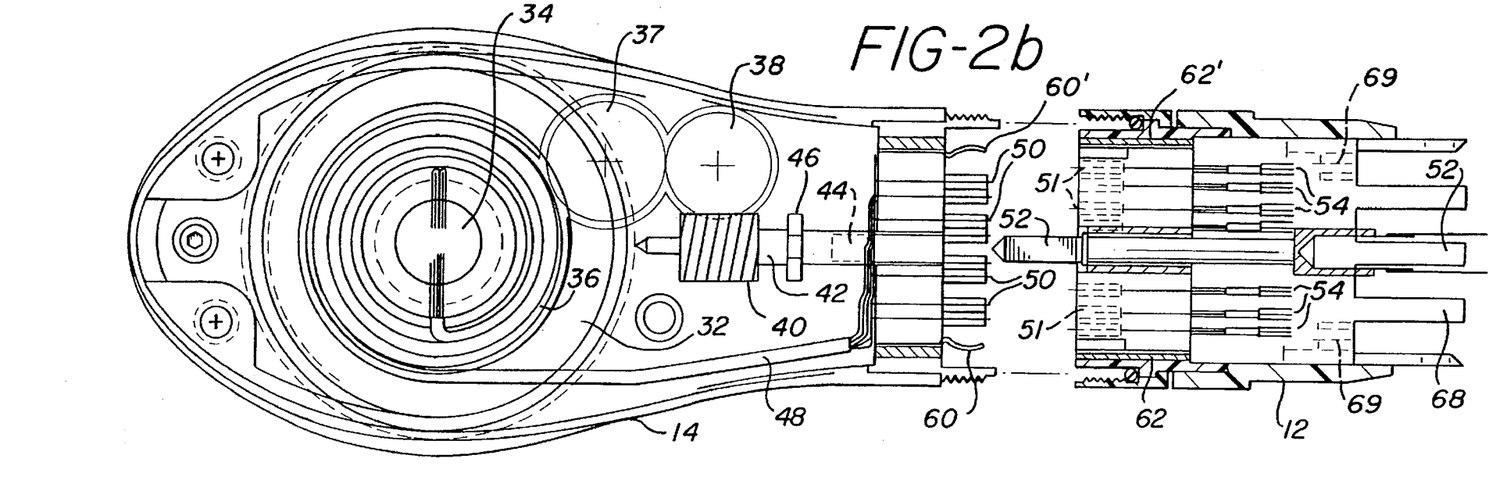
Figures 2C, 3:
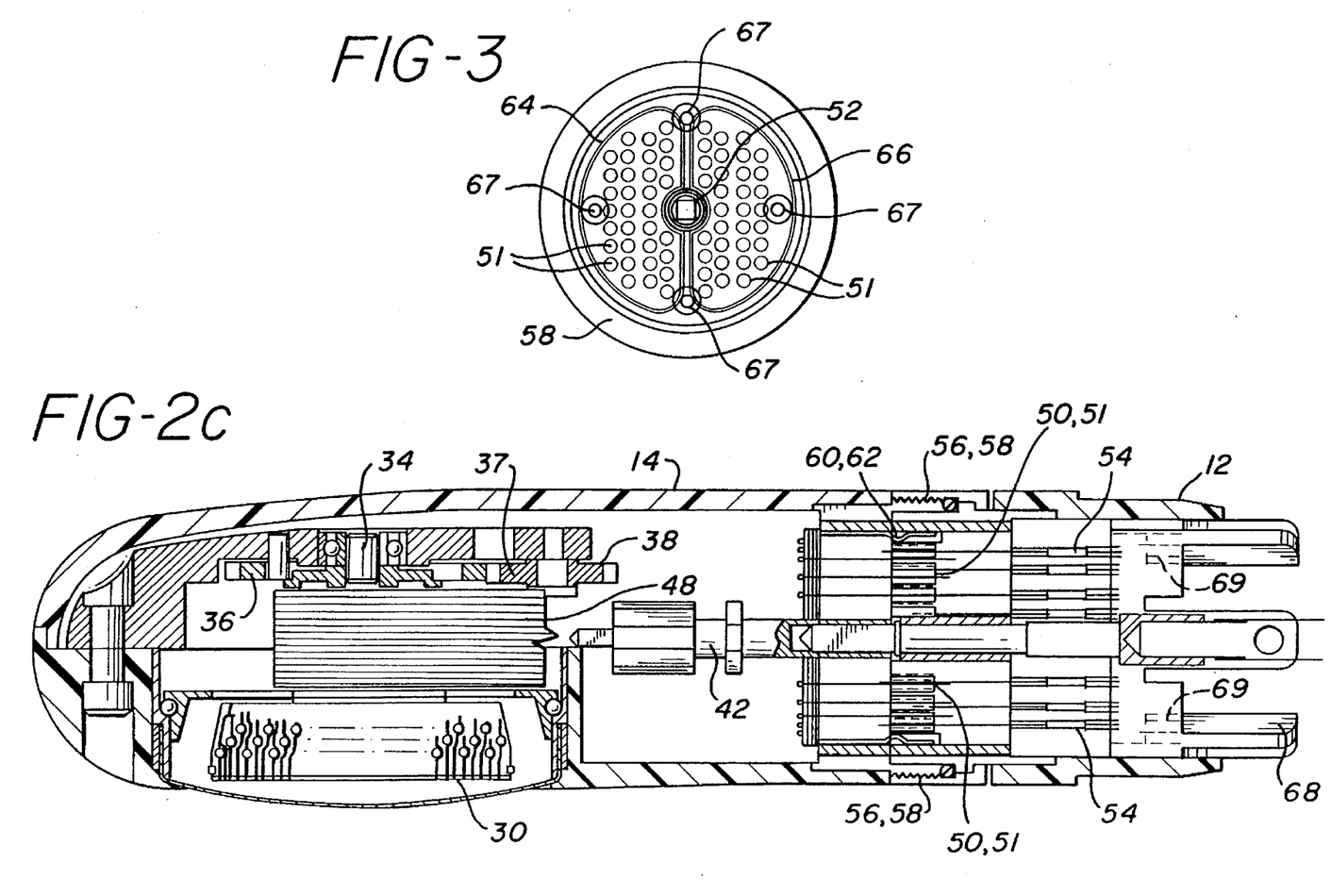

Referring now to FIGS. 2a–2c and 3, the distal tip of the probe is shown in greater detail. As FIGS. 2a and 2b show, the tip is detachable from the gastroscope tube 12 which enables the user to change transducers for different diagnostic procedures, for instance. The piezoelectric transducer 30 is shown in FIGS. 2a and 2c and is oriented for transmitting and receiving in the downward direction in those figures. Electrical signals are supplied to and from the transducer by a coiled flex circuit 48 which connects individual transducer elements to connector pins 50 at the proximal end of the distal tip. The coiling of the flex circuit prevents breaking of the electrical lines on the circuit with repeated flexing, as explained in U.S. Pat. No. 4,426,886. The transducer 30 is mounted in a rotating transducer cup 32. At the back of the cup is a shaft 34. A transducer drive gear 36 is mounted around the shaft 34. This drive gear is turned by the rotation of the distal tip drive shaft 42, the motion of which is transmitted to the drive gear by a worm gear 40, a worm wheel 38, and an intervening idler gear 37. The tip drive shaft 42 is held in place in the distal tip by a retaining ring 46. A square hole 44 is formed in the distal end of the tip drive shaft 42 to receive the gastroscope drive shaft 52.

The connector pins 50 at the distal end of the probe tip 14 mate with the sockets 51 at the distal end of the gastroscope tube. As the connector pins engage the sockets, the square end of the gastroscope drive shaft 52 engages the square hole 44 in the distal tip drive shaft 42 to rotate the transducer in its transducer cup 32. At the same time metallic spring pins 60, 60' engage the connector shields 62, 62' in the gastroscope to complete the electrical shielding of the connectors. If desired, one or more guide pins can be used between the distal tip and gastroscope tube to guide the mating of these connections. As the connections come together a threaded ring 58 on the gastroscope tube is threaded onto the threaded end 56 of the distal tip to fasten the two parts together. If desired, a locking mechanism can be employed on the threaded fittings to prevent unintentional detachment of the two parts.

The attachment of the distal tip 14 to the gastroscope tube 12 is shown in FIG. 2c. The connector sockets 51 are connected to individual coaxial wires 54, which transmit electrical signals to and from the transducer through the gastroscope, and ultimately to the connector 18 and the ultrasound system. Also shown in these figures is the distal end link 68 of the mechanism which articulates the distal tip of the probe.

FIG. 3 illustrates an end view of the gastroscope at several cross sectional planes, which shows the relative positioning of a number of components. The drive shaft 52 passes through the center of the gastroscope tube. At the end of the tube the connector sockets are seen to be arranged in two groups on respective sides of the tube. One group of connectors is contained within a "D" shaped brass shielding tube 64, and the other group is contained within a second brass shielding tube 66. The separate groupings reduce crosstalk during operation of the transducer in continuous wave Doppler mode. This is accomplished by connecting transmitting transducer elements through the connectors in one group, and receiving transducer elements through the connectors in the other group. By separating the two groups and providing separate shielding, crosstalk between the transmitting and receiving signal lines is reduced.

The articulation control cables pass through the gastroscope tube at positions indicated at 67 in FIG. 3. The ends of the cables are terminated at the points indicated at 69 in FIGS. 2a–2c.

Figure 6A:
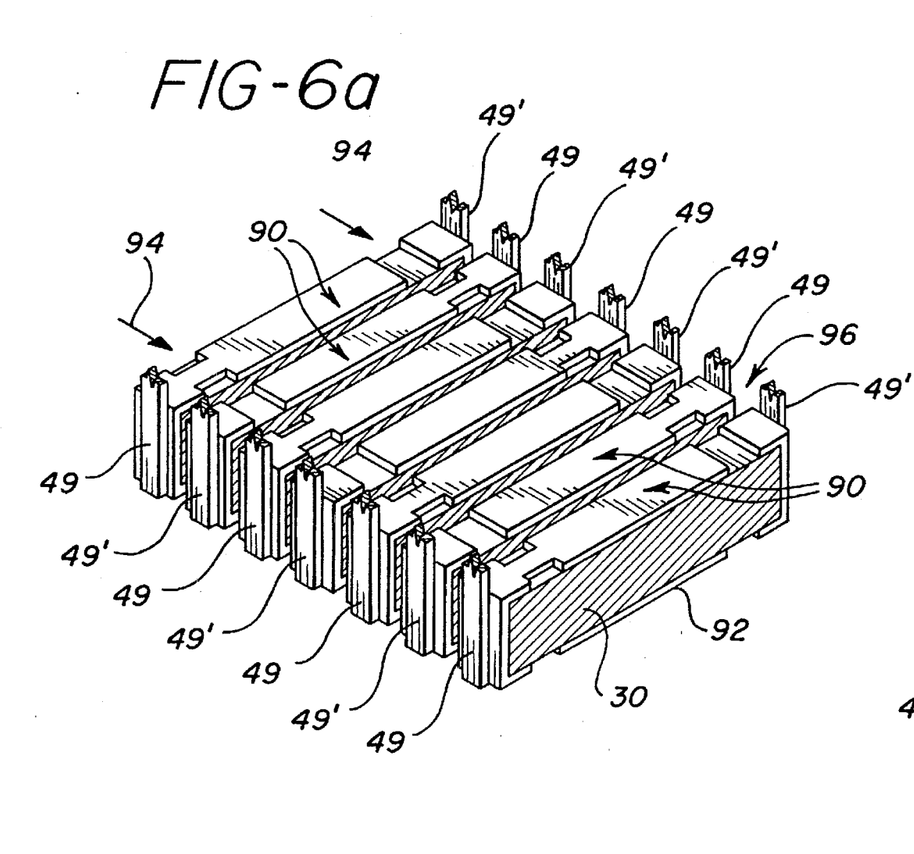
FIGS. 6a and 6b illustrate the construction of the ultrasonic array transducer and electrodes of the probe of FIG. 1.
Figure 6B:
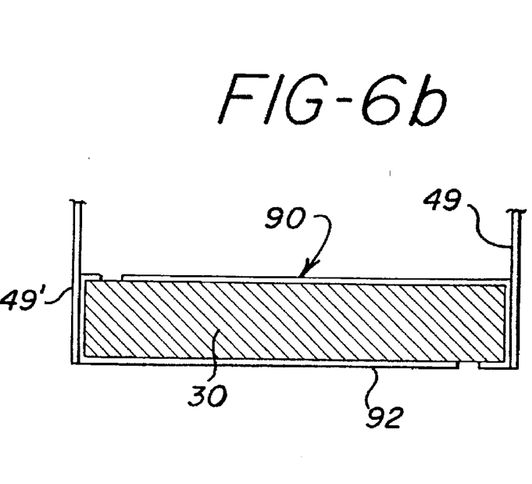

Enlarged views of the transducer 30 are shown in FIGS. 6a and 6b. A plate of piezoelectric ceramic 30 is initially covered on its two planar surfaces and edges with a metallized electrode coating. Laser cutting or photolithography is then used to form holes in the electrode coating in the longitudinal directions indicated by arrows 94. The ceramic plate and its metallized coating are then diced into individual transducer elements and electrodes by transverse dicing as indicated by arrow 96. The result is a series of transducer elements and electrodes as shown in FIGS. 6a and 6b. Signal electrodes 90 are located on one planar surface of the transducer 30 and wrap around one end of the transducer elements. Return electrodes 92 are located on the other planar surface of the transducer and wrap around the other end of the transducer elements as shown in FIG. 6a. Metallic fingers 49, 49' extending from the flex circuit 48 are attached to the electrodes at the ends of each element.

The laser formed cuts and notches result in an alteration of the signal and return ends of the transducer elements from one element to another. That is, metallic fingers 49 are connected to signal electrodes 90, and interspaced metallic fingers 49' are connected to return electrodes 92. The alternating patterns are offset from one end of the transducer to the other, since each signal finger must oppose a return finger on the other end of each element. The alternation of signal and return connections helps to reduce crosstalk between electrodes and connections.

Figure 7A:
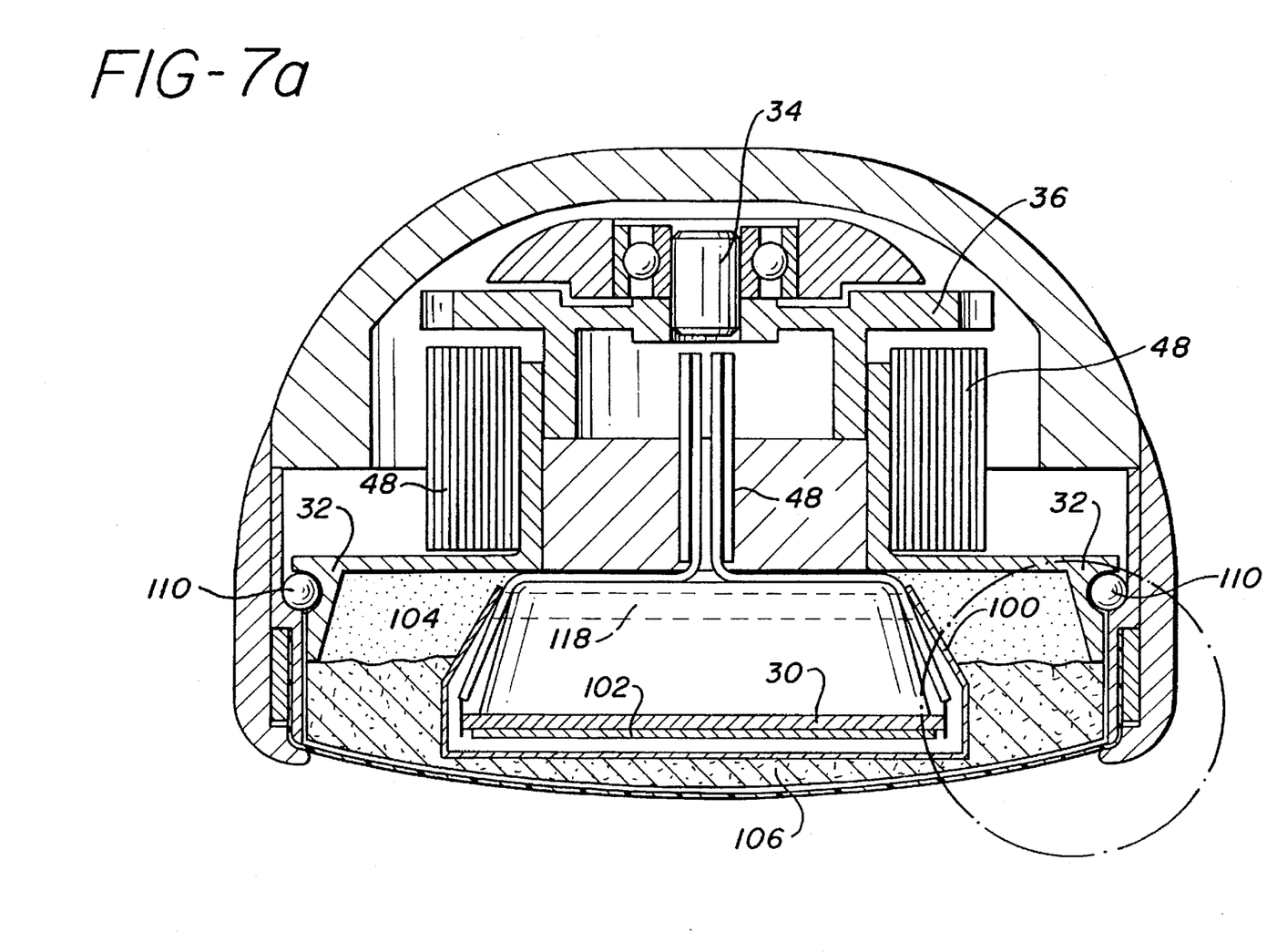
FIGS. 7a and 7b illustrate a technique for dissipating heat generated by the transducer at the tip of the probe of FIG. 1.
Figure 7B:
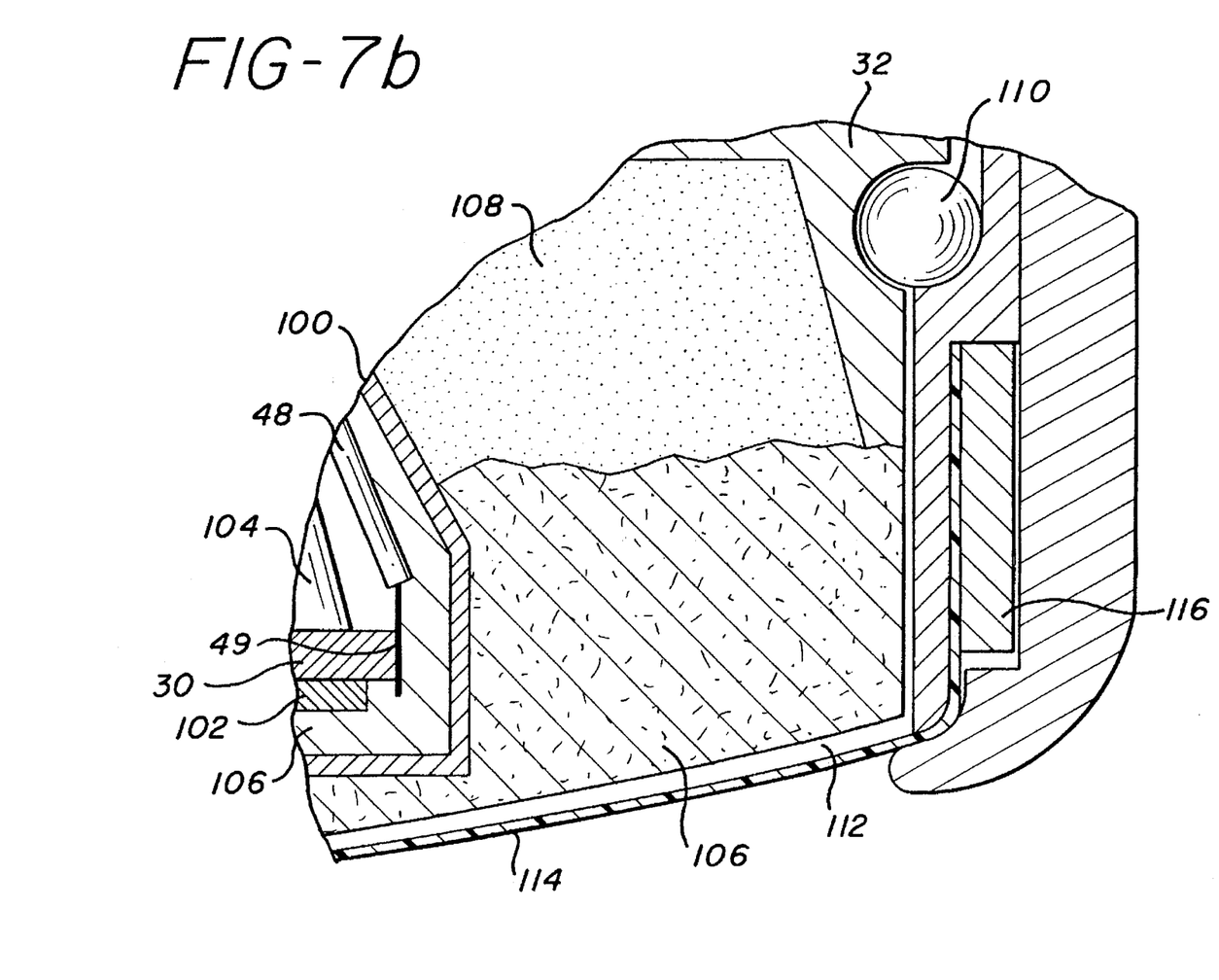

FIGS. 7a and 7b illustrate additional details of the construction of the transducer 30 in its transducer cup 32. FIG. 7b is an enlarged view of the circled area of FIG. 7a. The transducer 30 has a matching layer or layers 102 overlaying the transmitting surface of the transducer and is backed by backing material 104. The transducer 30 is completely encased within the transducer cup 32 by acoustic lens material 106 in the front and epoxy 108 in the back. A sheet 100 of aluminum foil is embedded in the lens material in front of the transducer 30 and extends to the rear of the transducer where it is attached to a heatsink 118. The transducer cup turns within its compartment in the distal end of the probe by moving against ball bearings 110 located around the periphery of the transducer cup 32. A mylar sheet 114 covers the front of the transducer cup and transducer and is held in place by a clamping ring 116. The inner surface of the mylar sheet is aluminized. A thin layer of oil fills the space between the lens material and the aluminized inner surface of the mylar cover.

The present inventors have found that most preferable lens materials have a low thermal conductivity. This causes heat buildup in the vicinity of the transducer. When only certain elements of the transducer are activated, as is generally the case with continuous wave Doppler, hot spots can develop in the vicinity of the active elements. The embedded aluminum foil sheet 100 in front of the transducer helps reduce such heat buildup by spreading out heat which develops at hot spots and conducting the heat trapped in the lens material to a heatsink mass behind the transducer and away from the patient contacting surface of the probe. Although a number of different metals may be used for the sheet 100, the present inventors prefer aluminum due to its high figure of merit for thermal/acoustic applications. Aluminum was chosen due to its high ratio of thermal conductivity to mass density, which makes it desirable for this application. Other materials with favorable ratios, such as graphite or superconductive material, may be preferred for other applications.

The aluminum layer in the inner surface of the cover 114 serves a like purpose. Heat which migrates to the front of the lens material is spread out and conducted to the sides of the transducer cup where it may be further dissipated into the housing structure surrounding the transducer cup. The combination of these two heat dissipating techniques has been found to enable prolonged use of the TEE probe within medically safe thermal limits.

Figures 4A, 4C:
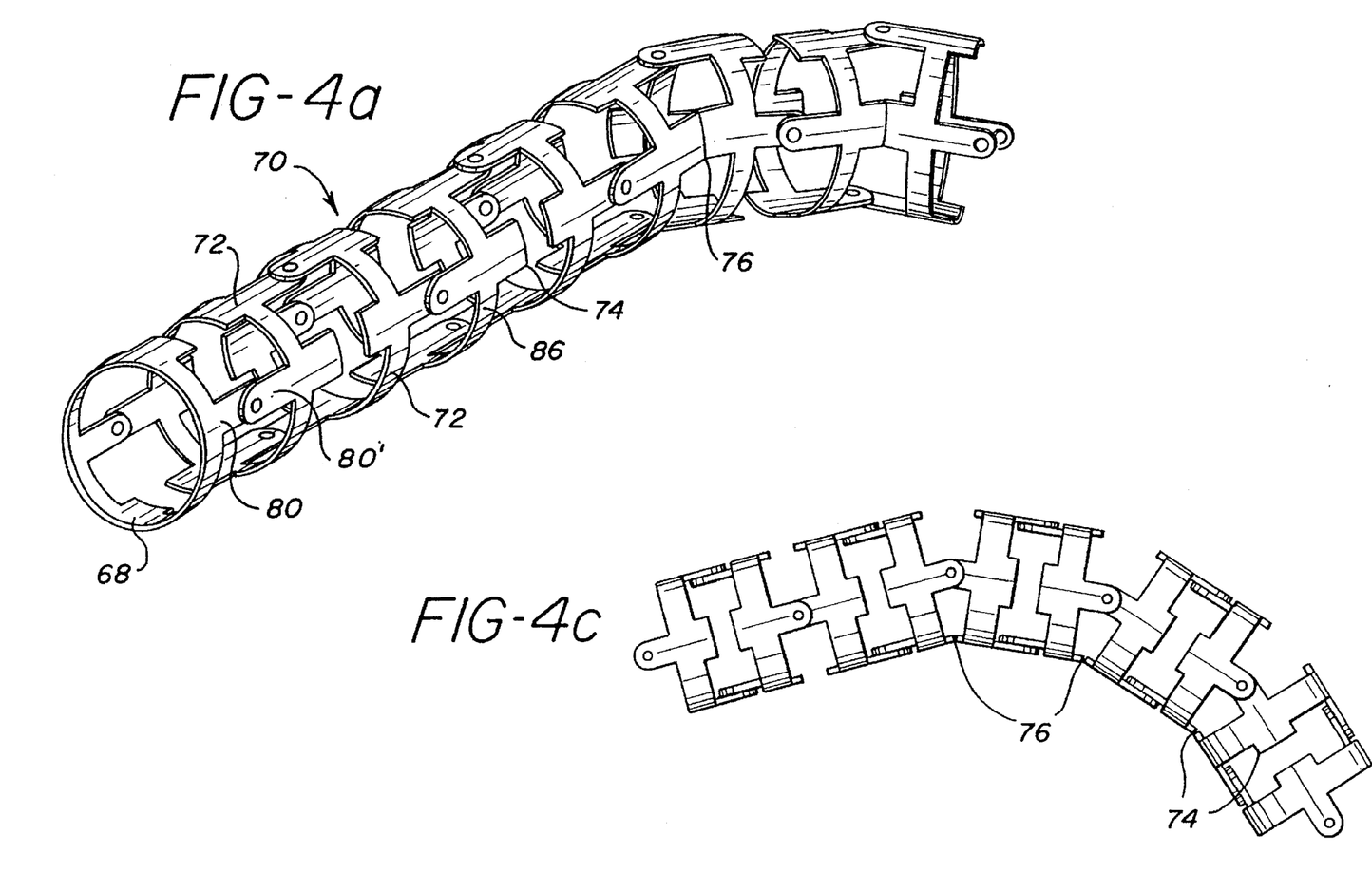
FIGS. 4a–4c and 5a–5c illustrate the articulating mechanism which enables articulation of the tip of the probe of FIG. 1.

Turning now to FIGS. 4a–4c and 5a–5c, the articulating mechanism 70 at the distal end of the gastroscope tube 12 is shown. FIG. 4a is a simple illustration of the interconnecting links of the mechanism 70. Each of the central links 72 is identical, and each links with an adjoining link by the relative 90° offset rotation from one link to the next. Specialized end links which connect at only one side, such as the end link shown at 68, may if desired by used at each end of the mechanism. The interconnection of opposing broad fingers 80 and 80' on opposite sides of the links causes each link to pivot relative to its neighbor, and successive pivot axes are oriented at 90° relative to each other. This means that when the articulating mechanism 70 is bent in one direction, the bending will occur by the pivoting of the mechanism at alternating axes between every other link. When the mechanism is bent at a second direction which is oriented 90° relative to the first, the intervening, alternating axes will pivot. At intervening orientations the bending causes all axes to pivot.

The interconnection of the links 72 in 90° alteration causes the intervening limit stop tabs 74 on opposite sides of the links to oppose each other. As the articulating mechanism is bent the limit stop tabs limit the pivoting from one link to the next. For instance, suppose each limit stop tab limited the pivoting to 10°. If the articulating mechanism is to be bent at a maximum angle of 90°, eighteen links would be needed, since pivoting in a given direction is provided by every other pivot axis, as FIG. 4c illustrates. The use of the limit stop tabs confines the bend from one link to another to an angle suitable for the application, including maintenance of desired dimensions of the passageway through the center of the links, which in the TEE probe application carries electrical wiring, a transducer drive shaft, and articulation control cables.

Figure 4B:
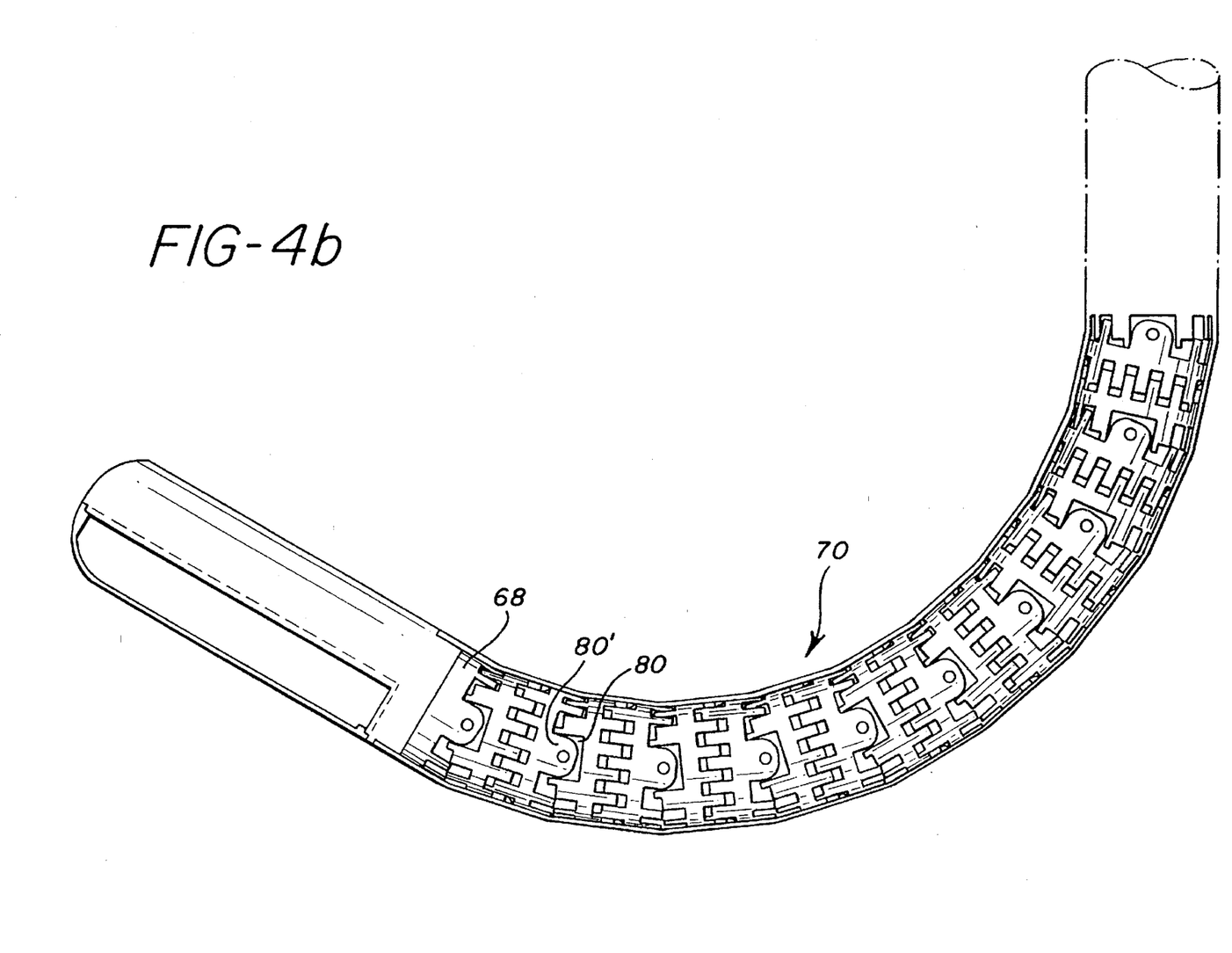
Figure 5A:
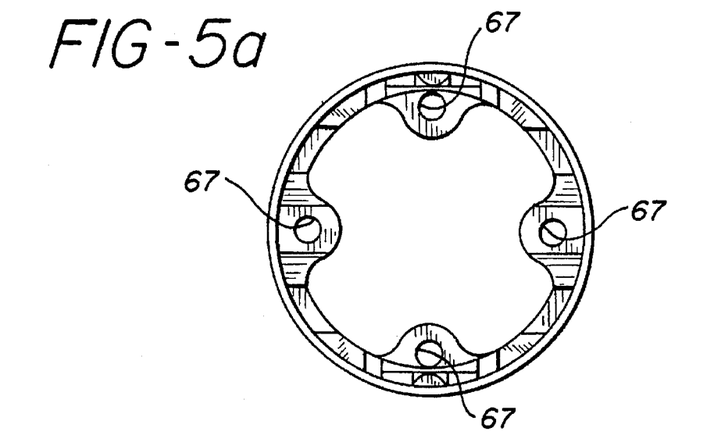
Figure 5B:
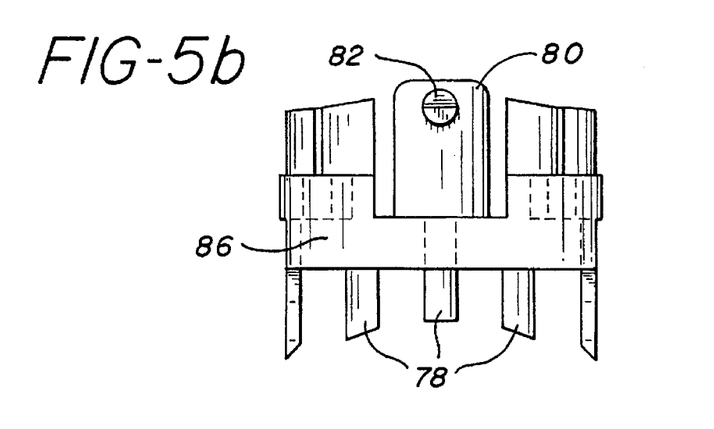
Figure 5C:
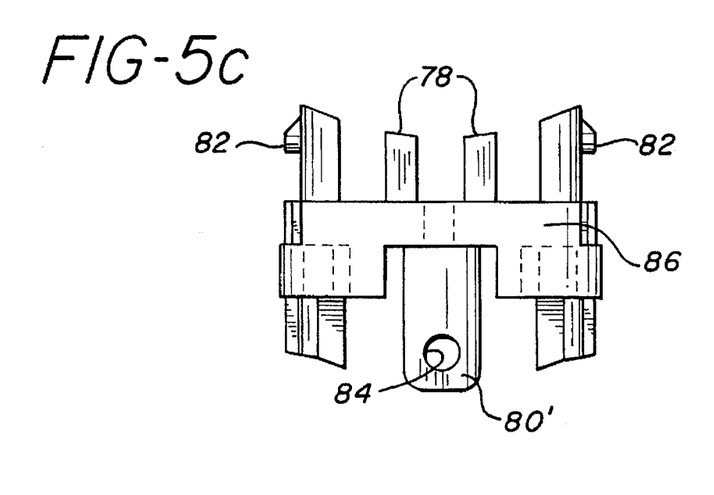

FIG. 4b and FIGS. 5a–5c show the preferred embodiment of the limit stop tabs, which are formed of thin fingers 78 which mesh with the thin fingers of the opposing link. The limit stop is attained when the thin fingers of one link mesh with the thin fingers of the opposing link, and the end of each finger contacts the main body 86 of the opposing link. FIGS. 5a–5c also show the broad fingers 80, 80' of each link. Broad fingers 80, located on opposite sides at one end of each link, carry protruding studs 82. Broad fingers 80', located 90° around each link with respect to fingers 80, each have a hole 84 which engages a stud from an interconnecting link. The meshing fingers and interconnecting holes and studs have been found to provide the articulating mechanism 70 with exceptional torsional stiffness. This torsional stiffness prevents twisting of the probe tip relative to the gastroscope tube as the probe is turned inside the body by the physician.

FIG. 5a shows a number of projections located around the inner periphery of the central body 86 of each link, with each projection having a hole 67. When the links are interconnected the holes 67 of the mechanism are in alignment and carry the articulation control cables of the gastroscope.

In addition to torsional stiffness, the articulating mechanism 70 exhibits substantially no torsional play when loaded by the tightening or braking of the articulation control cables. Thus the articulating mechanism will maintain its shape without twisting as the probe tip is bent and locked in various positions. The links of the articulating mechanism snap together easily by locating the studs 82 in the holes 84. The links are made of brass or preferably stainless steel to provide electrical shielding for the wires contained inside and a long wear life for the articulating mechanism. Furthermore, the preferred fingers have been found to form a substantially continuous supporting surface along the outer surface of the articulating mechanism, as shown in FIG. 4b. The surface has been found to be capable of carrying a sheath covering while still bending readily without binding or pinching the outer sheath.

Figure 8A:
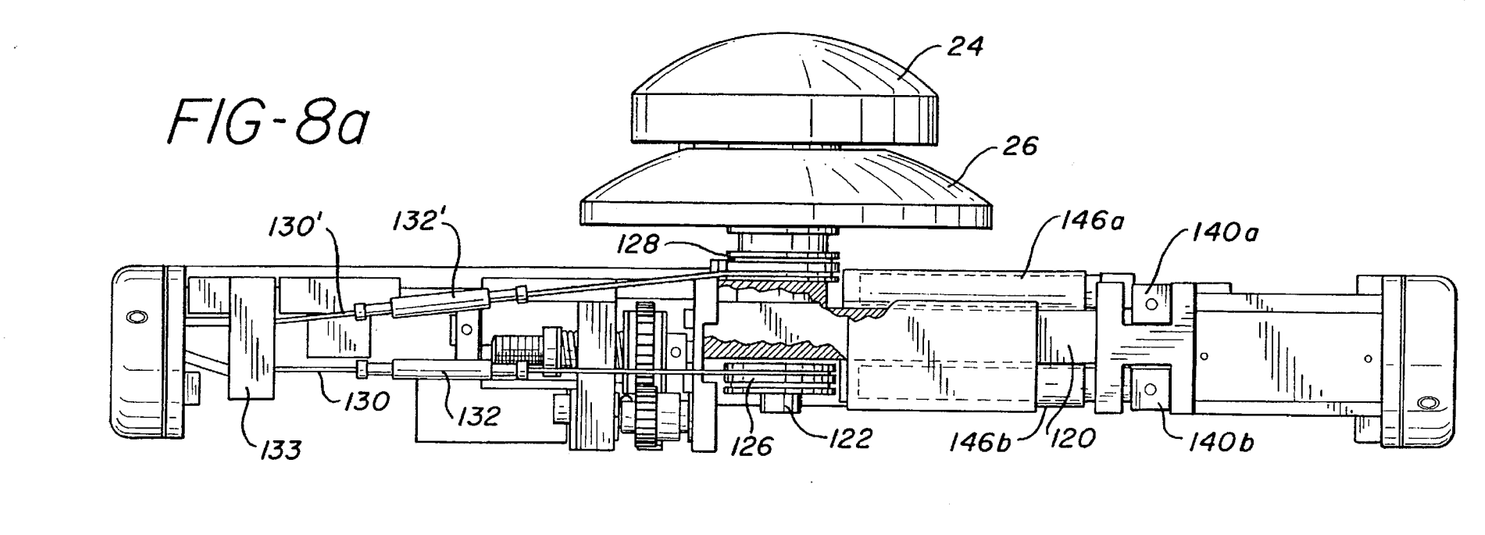
FIGS. 8a and 8b illustrate the mechanism within the handle of the probe of FIG. 1 which is used to control probe tip articulation and transducer rotation.
Figure 8B:
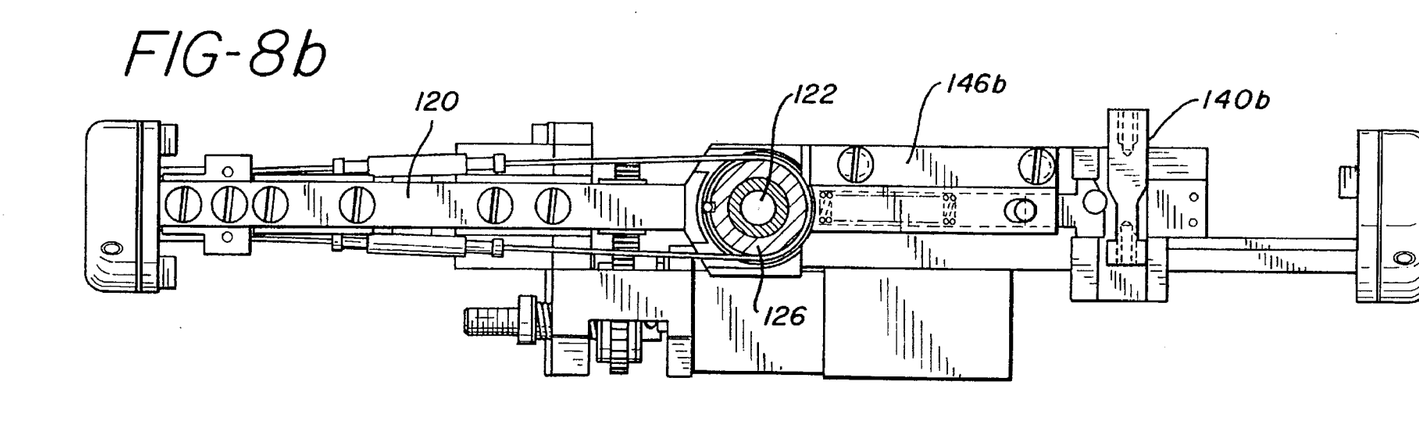
Figure 9:
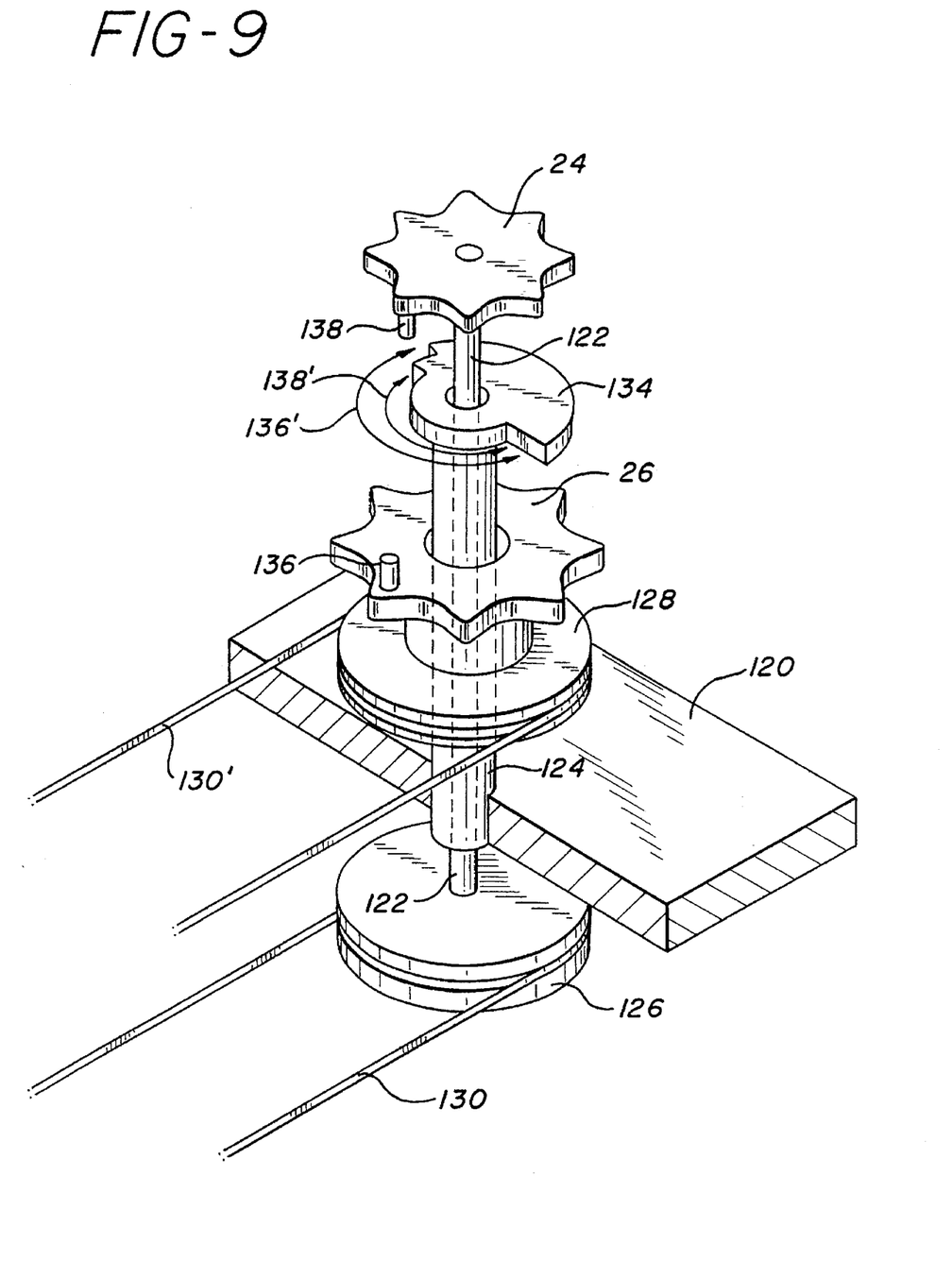
FIG. 9 illustrates the control knobs and limit stops for the articulation control mechanism of FIGS. 8a and 8b.

The articulation control mechanism, located within the handle 10, is shown in FIGS. 8a and 8b and FIG. 9. The components of the handle 10 are mounted on a longitudinal chassis 120 contained within the handle case. The right-left control knob 24 is connected by a shaft 122 to the right-left pulley 126. A control cable 130 is wrapped around the pulley 126 and extends through a cable bracket 133, through the gastroscope tube 12, and through opposing aligned holes 67 of the articulating mechanism 70 to attachment points 69 at the distal end of the gastroscope.

Similarly, the forward-back control knob 26 is attached to forward-back pulley 128. A cable 130' is wrapped around the pulley 128 and likewise extends through the cable bracket 133, the gastroscope tube 12, the other pair of opposing aligned holes 67 of the articulating mechanism to the cable attachment points 69. A turnbuckle 132, 132' is located in line with each cable to adjust cable tension.

The shaft 122 is carried inside of a tube 124 which is attached to the chassis 120 of the probe. The tube 124 passes through the center of the knob 26 and pulley 128 and has a limit stop cam 134 attached at the end of the tube, between the two control knobs. A limit stop pin 138 extends down from the right-left control knob 24 and travels in a path 138' at knob 24 is turned. Similarly, a limit stop pin 136 extends upward from the forward-back control knob 26 and travels in a path 136' as knob 26 is turned. Travel paths 136' and 138' are seen to be different, in correspondence with the desired range of articulation to be controlled by each respective knob. In TEE probes of the prior art the articulation limit stops are located at the distal end of the endoscope tube. If the physician should overstress the cables or turn the control knobs too far, the distally located limit stops can be overstressed or fail, resulting in damage to the TEE probe, injury to the patient, or both. FIG. 9 shows that the limit stops are preferably located in the handle, with the limits imposed by the chassis of the handle itself. When the control knobs are turned against these limit stops, the continued application of force will be applied to the handle and not to the distal end of the endoscope, thereby reducing the possibilities of damage to the TEE probe and patient injury.

Figure 10:
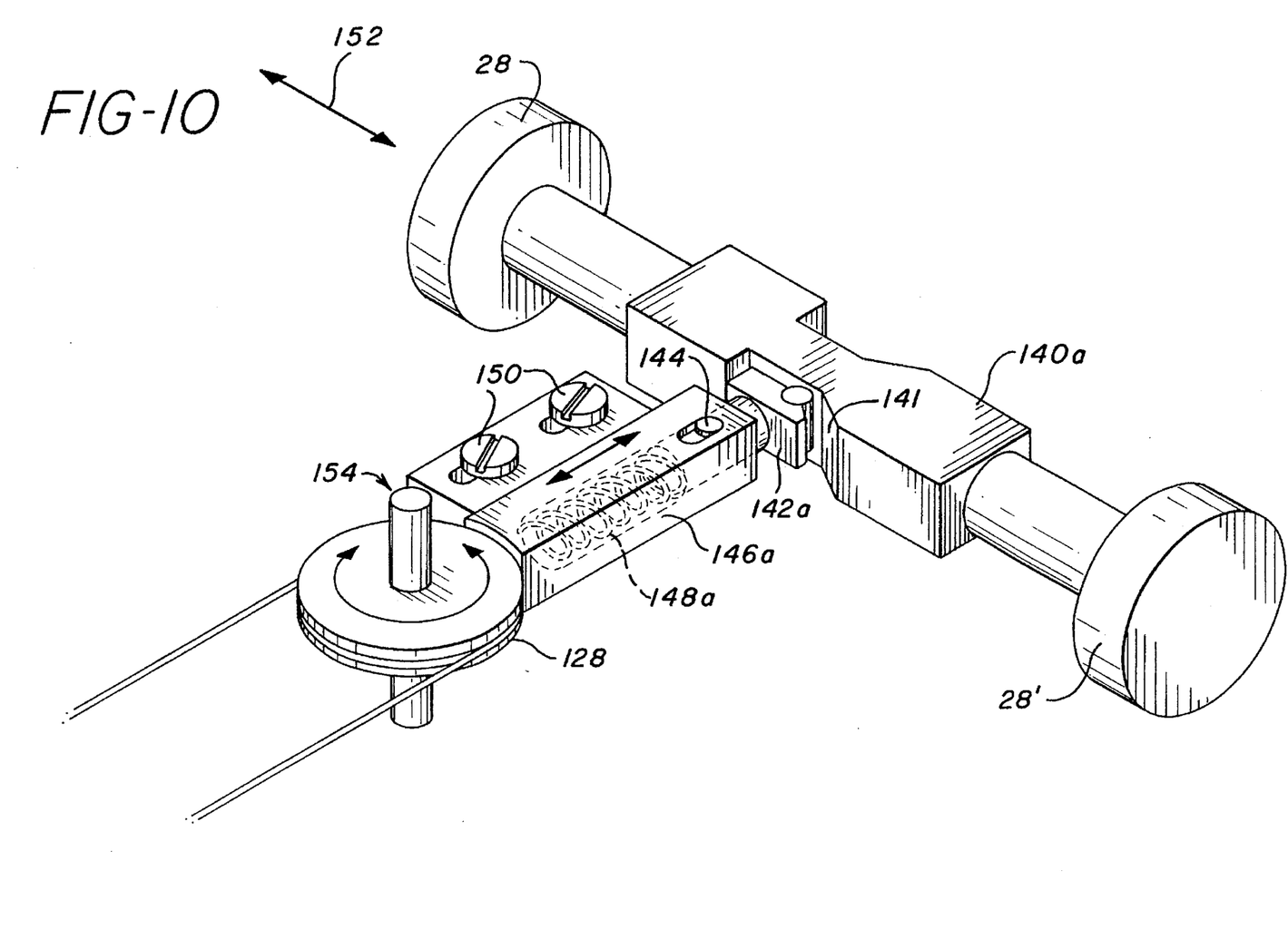
FIG. 10 illustrates the brake system for the articulation control mechanism of FIGS. 8a and 8b.

FIGS. 8a, 8b and 10 illustrate the brake for the articulating mechanism 70. The physician will manipulate the control knobs 24 and 26 until the tip of the probe has been articulated to a position where it is desired to gather ultrasonic information from within the patient. When the transducer is properly positioned the physician wants to lock the articulating mechanism in its current position. A brake is provided for each articulation orientation to fill this purpose.

A first brake is provided for the right-left pulley 126 and a second brake is provided for the forward-back pulley 128. A pair of lock buttons 28' for the brakes extend out from one side of the handle 10 and a pair of unlock buttons 28 extend from the other side of the handle. Depressing the lock button 28' will move a reciprocating articulation brake cam 140a or 140b in the direction indicated by arrow 152. The cam surface 141 of the respective cam will then exert pressure against a respective cam follower 142a or 142b of a brake slide 146a or 146b, each of which is attached to the chassis of the handle by sliding posts 150. The brake slides are preloaded with a spring 148a or 148b and the cam followers are connected by a pin 144a or 144b that allow the cam followers to move against the springs. As the brake is moved to its full locked position, the brake slide will move approximately 0.030 inches and exert a force of approximately 18 pounds against the pulley.

As the brake slide moves against the pulley it also presses against and closes a pressure sensitive switch located at 154 in FIG. 10. Closure of the switch signals that the lock is engaged, and lights an LED light on the handle, such as the LED handle indicators shown in U.S. Pat. No. 5,050,610. The switch signal is also connected through the connector 18 to the ultrasound system to cause a message, "BRAKE ON", to be displayed on the ultrasound system display. These two indicators, one on the ultrasound system display and another on the TEE probe handle, warn the physician that the brake is engaged and the probe tip is locked in some articulated position. This warning is intended to alert the physician not to remove the TEE probe from the patient's body until the brake has been disengaged, as removal of the TEE probe with the tip bent in some curved position may cause irritation of the esophagus or other injury to the patient or probe.

However, the TEE probe of the present invention has been designed to prevent injury due to removal of a TEE probe locked in an articulated position. The present inventors have found that 18 pounds of force, applied to the pulleys as a brake, can be overcome by application of significantly lesser force to the end of an articulated probe. Thus, if the probe is removed in a locked, articulated position, the small force of the esophagus wall pressing against the tip of the probe, combined with the leverage of the bent tip, will overcome the braking force and straighten out the probe. The probe will be removed from the patient with little or no irritation to the patient, even when the probe is removed in a locked, articulated position.

Figure 11:
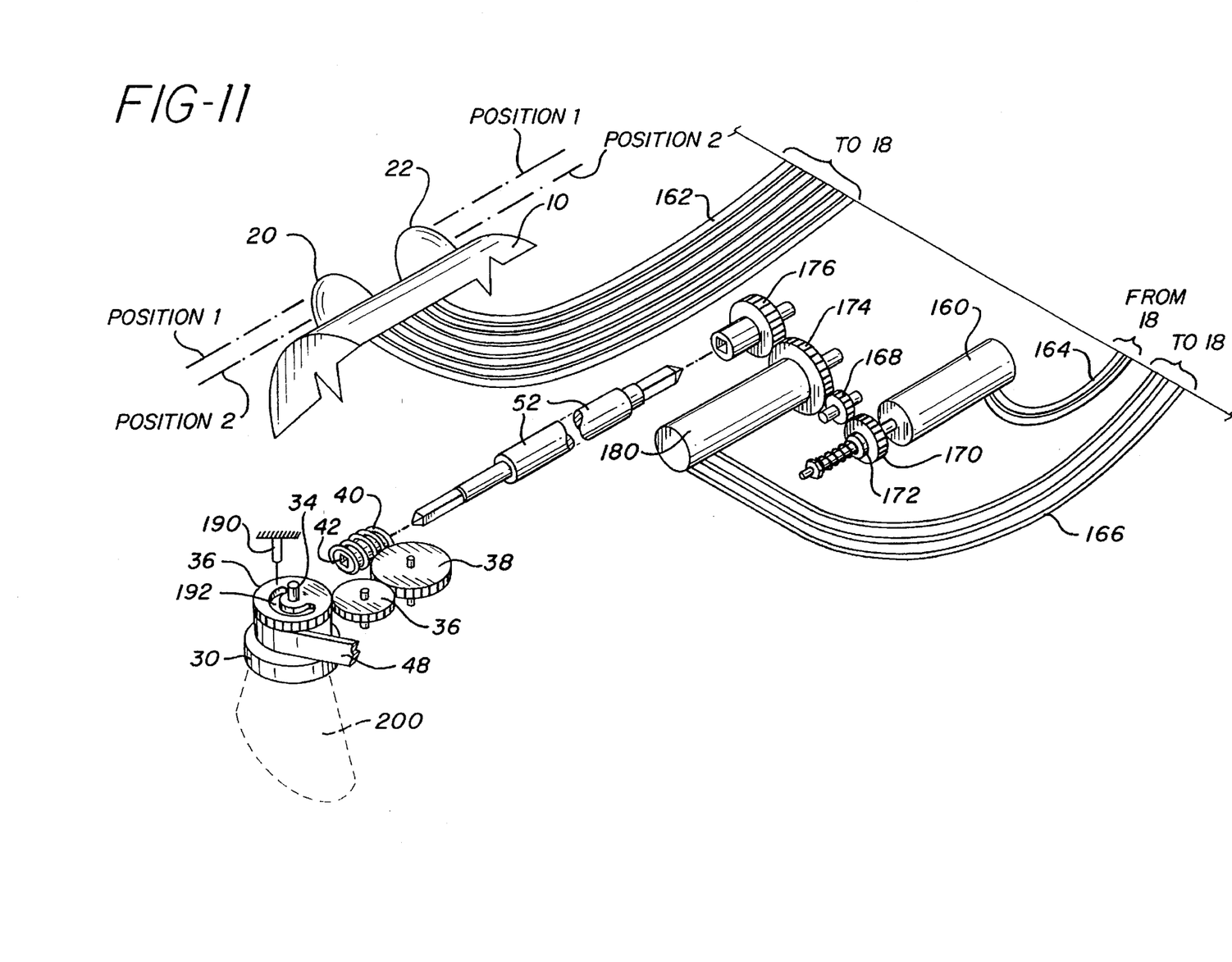
FIG. 11 illustrates the motor control linkage for rotating the transducer in the tip of the probe.

The rotation control system for the transducer is shown in FIGS. 8a, 8b and 11. Each of the transducer rotation buttons 20 and 22 is a three position switch. The normal position is off, the first detent is position 1, and the second detent is position 2. When a switch is depressed to the first detent position the transducer will rotate slowly. If switch 20 is depressed this rotation will be in the clockwise direction, and if switch 22 is depressed the rotation will be in the counterclockwise direction. Depressing a switch to the second detent position will result is more rapid rotation of the transducer in either the clockwise or counterclockwise direction.

The various states of the switches 20 and 22 are transmitted to the ultrasound system through wires 162 and connector 18, interpreted and converted to motor drive signals for motor 160, which are applied through the connector 18 and wires 164. The motor is driven clockwise, counterclockwise, slow, or fast.

Rotation of the motor shaft is transmitted through a slip clutch 172 to a gear 170. The gear 170 turns an idler gear 168 which in turn rotates a gear 174. Gear 174 is connected to the shaft of a potentiometer 180, and also turns gear 176 at the end of the drive shaft 52. The rotation of the drive shaft turns the worm gear 40, worm wheel 38, idler gear 37, transducer drive gear 36, the transducer cup 32 shaft 34 and finally the transducer cup and transducer 30. In this way the image plane 200 of the transducer is turned inside the body of the patient.

As the shaft of potentiometer 180 turns in synchronism with the motor, it sends signals through wires 166 to the ultrasound system, which are interpreted to indicate the relative orientation of the image plane 200. This orientation information is generally indicated on the ultrasound system display as described in U.S. Pat. No. 5,207,225.

The transducer drive gear 36 is seen to have an arcuate opening 192 which engages a limit stop pin 190 for the transducer rotation. The limit stop pin 190 and opening 192 thereby limit the extent of transducer rotation in both directions. If the user continues to drive the motor 160 with the limit stop at the end of its range, the friction of the slip clutch 172 will be overcome. The motor will continue to turn but the motor gear train will not turn due to operation of the slip clutch 172.

Finally, the rotating transducer and image plane are given a predetermined nominal, or "home", orientation. Generally this orientation is with the image plane 200 aligned parallel or perpendicular to the unbent tube of the gastroscope. When both buttons 20 and 22 are depressed simultaneously the ultrasound system commands the motor 160 to rotate the transducer to this home position. The ultrasound system monitors the signals from potentiometer 180 as the transducer is rotated in the appropriate direction to cause the signals from the potentiometer to converge on the signal indicative of the home position. If the physician notes something in the image while this home rotation is ongoing, or decides to again control rotation incrementally, depressing any switch while in the home position sequence will end the sequence and return normal control of the buttons 20 and 22 to the physician.

What is claimed is:

1. An ultrasonic transducer probe having a piezoelectric transducer located at a distal end thereof for ultrasonic scanning from within a cavity of the body, said transducer being movable with respect to said distal end to change the scan plane orientation, comprising:

a control section for controlling the movement of said transducer including means for selectively changing said scan plane orientation;

an endoscope tube section connecting said distal end and said control section;

electrical wiring, electrically extending from said control section to said distal end through said endoscope tube section and coupled to said transducer, for supplying energizing signals to said transducer and conveying ultrasonic signals received by said transducer to an ultrasonic signal processing system; and a connector for disconnecting said distal end from, and reconnecting said distal end to, said endoscope tube section, including means for removably connecting electrical wiring in said distal end to electrical wiring in said endoscope tube section, and means for removably connecting said means for selectively changing said scan plane orientation.

2. The ultrasonic transducer probe of claim 1, wherein said connector comprises means for allowing the transducer of the probe to be changed for different diagnostic procedures.

3. The ultrasonic transducer probe of claim 2, wherein said connector includes a plurality of electrical connections for coupling said electrical wiring between said distal end and said endoscope tube section.

4. The ultrasonic transducer probe of claim 1, wherein said means for rotating said transducer comprises a transducer drive shaft located in said endoscope tube, and said connector includes a keyed drive shaft aperture for transferring the drive energy of said drive shaft to said distal end.

5. An ultrasonic transducer probe having a piezoelectric transducer comprising an array of linear transducer elements located at a distal end thereof for ultrasonic scanning from within a cavity of the body, said transducer being rotatable with respect to said distal end to change the scan plane orientation, comprising:
- a control section for controlling the movement of said transducer including means for selectively changing said scan plane orientation;
- an endoscope tube section connecting said distal end and said control section;
- electrical wiring, electrically extending from said control section to said distal end through said endoscope tube section and coupled to individual elements of said transducer, for supplying energizing signals to said transducer and conveying ultrasonic signals received by said transducer to an ultrasonic signal processing system; and
- a connector for disconnecting said distal end from, and reconnecting said distal end to, said endoscope tube section, including means for removably connecting electrical wiring of said elements of said transducer in said distal end to electrical wiring in said endoscope tube section, and means for removably connecting said means for selectively changing said scan plane orientation.

6. The ultrasonic transducer probe of claim 5, wherein said means for removably connecting electrical wiring comprise a plurality of mating pins and sockets located in mating sections of said connector.

7. An ultrasonic transducer probe having a piezoelectric transducer located at a distal end thereof for ultrasonic scanning from within a cavity of the body, said transducer being rotatable with respect to said distal end, comprising:
- a manual control section for controlling the rotation of said transducer;
- an endoscope tube section connecting said distal end and said control section;
- electrical wiring, electrically extending from said control section to said distal end through said endoscope tube section and coupled to said transducer, for supplying energizing signals to said transducer and conveying ultrasonic signals received by said transducer to an ultrasonic signal processing system; and
- a connector for disconnecting said distal end from, and reconnecting said distal end to, said endoscope tube section, including means for removably connecting electrical wiring in said distal end to electrical wiring in said endoscope tube section, and means for removably connecting a means for rotating said transducer between said distal end and said endoscope tube section:
- wherein said means for removably connecting electrical wiring comprise a plurality of mating pins and sockets located in mating sections of said connector: and
- wherein said connector further comprising means for electrically connecting connector shielding in said endoscope tube section to connector shielding in said distal end.

8. The ultrasonic transducer probe of claim 6, wherein said connector further comprises a drive shaft for rotating said transducer and a keyed aperture for connecting said drive shaft between said endoscope tube section and said distal end.

9. The ultrasonic transducer probe of claim 5, wherein said connector further comprises guide pin means for guiding the mating of said distal end to said endoscope tube section.

10. The ultrasonic transducer probe of claim 5, wherein said connector further comprises a threaded fitting for removably connecting said distal end to said endoscope tube section.

11. The ultrasonic transducer probe of claim 10, wherein said threaded fitting further includes a locking mechanism for preventing unintentional detachment of said distal end from said endoscope tube section.

12. The ultrasonic transducer probe of claim 10, wherein said threaded fitting further includes a gasket for providing a watertight fitting when said distal end is attached to said endoscope tube section.

13. An ultrasonic transducer probe having a piezoelectric transducer located at a distal end thereof for ultrasonic scanning from within a cavity of the body, said transducer being rotatable with respect to said distal end, comprising:
- a control section for controlling the rotation of said transducer;
- an endoscope tube section connecting said distal end and said control section;
- electrical wiring, electrically extending from said control section to said distal end through said endoscope tube section and coupled to said transducer, for supplying energizing signals to said transducer and conveying ultrasonic signals received by said transducer to an ultrasonic signal processing system; and
- a connector for connecting said distal end to said endoscope tube section, including two separately shielded groups of electrical wiring connected to said transducer for sending transmitting signals to said transducer through the wiring of one group and sending received signals from said transducer through the wiring of the other group during continuous wave Doppler operation of said probe.

14. The ultrasonic transducer probe of claim 13, wherein said electrical wiring in said endoscope tube section comprises coaxial wires.

15. The ultrasonic transducer probe of claim 14, wherein said electrical wiring in said distal end comprises flex circuit.

16. An ultrasonic transducer probe having a piezoelectric transducer comprising an array of transducer elements located at a distal end thereof for ultrasonic scanning from within a cavity of the body, comprising:
- a control section for controlling the movement of said distal end;
- an endoscope tube section connecting said distal end and said control section;
- coaxial electrical wiring, electrically extending from said control section to said distal end through said endoscope tube section and coupled to said transducer, for supplying energizing signals to said transducer and conveying ultrasonic signals received by said transducer to an ultrasonic signal processing system; and
- a connector for disconnecting said distal end from, and reconnecting said distal end to, said endoscope tube section, including means for removably connecting electrical wiring in said distal end to said coaxial wires in said endoscope tube section.

* * * * *